United States Patent [19]

Hoelderich et al.

[11] Patent Number: 4,906,758

[45] Date of Patent: Mar. 6, 1990

[54] PREPARATION OF PYRROLES FROM DIALKOXYTETRAHYDROFURANS

[75] Inventors: Wolfgang Hoelderich, Frankenthal; Michael Hesse, Ludwigshafen; Hardo Siegel, Speyer, all of Fed. Rep. of Germany

[73] Assignee: BASF Aktiengesellschaft, Ludwigshafen, Fed. Rep. of Germany

[21] Appl. No.: 231,259

[22] Filed: Aug. 12, 1988

[30] Foreign Application Priority Data

Aug. 14, 1987 [DE]  Fed. Rep. of Germany ....... 3737114

[51] Int. Cl.$^4$ ................... C07B 43/04; C07D 207/323
[52] U.S. Cl. ..................................... 548/560; 548/563; 548/564
[58] Field of Search ........................ 548/560, 563, 564

[56] References Cited

U.S. PATENT DOCUMENTS

| | | | |
|---|---|---|---|
| 3,008,965 | 11/1961 | Zellner | 548/560 |
| 3,869,554 | 3/1975 | Pittet | 548/560 |
| 3,980,089 | 9/1976 | Pittet et al. | 131/144 |
| 3,984,436 | 10/1976 | Jaegal | 548/563 |
| 4,278,685 | 7/1981 | Ward | 548/561 |
| 4,492,710 | 1/1985 | Nerkel | 548/427 |
| 4,560,769 | 12/1985 | Menig et al. | 548/560 |
| 4,563,477 | 1/1986 | Maldonado | 548/562 |

OTHER PUBLICATIONS

Flanigan, Pure I. Appl. Chem. 58, 1351(1986).
Murai, J. Amer Chem. Soc. 106, 6093(1984).

*Primary Examiner*—Mark L. Berch
*Attorney, Agent, or Firm*—Keil & Weinkauf

[57] ABSTRACT

Pyrroles of the formula I

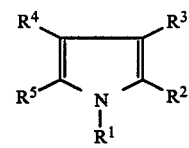

are prepared by a process in which a dialkoxytetrahydrofuran of the formula II

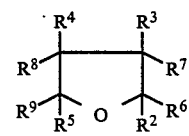

where $R^2$ to $R^5$ in the formulae (I) and (II) are identical or different and are each hydrogen, a straight-chain or branched alkyl or alkenyl radical of not more than 12 carbon atoms, a cycloalkyl or cycloalkenyl radical of 5 to 8 carbon atoms, an aryl, alkylaryl or aralkyl radical of 6 to 16 carbon atoms, and two non-adjacent radicals $R^6$ to $R^9$ are alkoxy and the other two radicals $R^6$ to $R^9$ are hydrogen, is reacted with ammonia or a primary amine $H_2NR^1$, where $R^1$ in formula (I) is hydrogen, alkyl, aryl, alkylaryl, aralkyl or cycloalkyl, in the presence of an acidic, solid, heterogeneous catalyst. Zeolites, for example those of the pentasil type or faujasite type, or phosphates, acidic oxides, phosphoric acid or boric acid on a carrier can be used as the solid heterogeneous catalysts.

10 Claims, No Drawings

PREPARATION OF PYRROLES FROM DIALKOXYTETRAHYDROFURANS

The present invention relates to a process for the preparation of pyrroles by reacting a dialkoxytetrahydrofuran with ammonia or a primary amine in the presence of an acidic, solid heterogeneous catalyst.

There are many possible methods for the synthesis of pyrroles (J. M. Patterson, Synthesis 281 (1976); E. Baltazzi and L. J. Kirmen, Chem. Rev. 63 (1963), 511). The syntheses due to Paal and Knorr, to Knorr and to Hantzsch are particularly important for the preparation of C-substituted pyrroles (A. H. Jackson, Compr. Chem. -4 (1979), 275–320). N-alkyl-substituted pyrroles can be prepared by catalytic dehydrogenation of the corresponding pyrrolidines over $Pd/Al_2O_3$ catalysts (U.S. Pat. No. 3,008,965 and European Patent No. 67,360). The preparation of pyrroles from 2-butenediols and ammonia or primary amines in the presence of supported catalysts containing Cu, Ag, Zn, Pd, Ni and Co is also known (European Patent No. 125,415).

Furthermore, Acta Chem. Scan. -6 (1952), 667–670, J. Org. Chem. 27 (1962), 2466–2470 and U.S. Pat. No. 3,980,089 disclose that some dimethoxytetrahydrofurans react with certain primary amines to give pyrroles, and the reaction has to be carried out in acetic acid.

We have found that pyrroles of the formula I

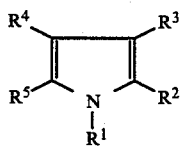

are obtained if a dialkoxytetrahydrofuran of the formula II

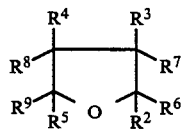

where $R^2$ to $R^5$ in the formulae (I) and (II) are identical or different and are each hydrogen, a straight-chain or branched alkyl or alkenyl radical of not more than 12 carbon atoms, a cycloalkyl or cycloalkenyl radical of 5 to 8 carbon atoms, or an aryl, alkylaryl or aralkyl radical of 6 to 16 carbon atoms, and two non-adjacent radicals $R^6$ to $R^9$ are alkoxy and the other two radicals $R^6$ to $R^9$ are hydrogen, is reacted with ammonia or a primary amine $H_2NR^1$, where $R^1$ in formula (I) is hydrogen, alkyl, aryl, alkylaryl, aralkyl or cycloalkyl, in the presence of an acidic, solid heterogeneous catalyst.

Compared with the prior art, the novel process gives pyrroles in a good yield and purity and with a good space-time yield in a simple and economical manner. Furthermore, the amounts of catalyst required are smaller. The process according to the invention is particularly suitable for continuous operation on an industrial scale. All the advantages mentioned are surprising, for example the fact that high selectivities and yields are achieved the novel reaction in the gas phase, since polymerization of the pyrroles was expected at high temperatures. There are also no corrosion problems due to acetic acid.

Suitable radicals $R^2$ to $R^5$, independently of $R^1$, are hydrogen and straight-chain or branched alkyl or alkenyl radicals of 1 to 12, in particular 1 to 8, preferably 1 to 4, carbon atoms.

Alkyl is, for example, methyl, ethyl, propyl, nbutyl, isobutyl, pentyl, hexyl, octyl or decyl. Alkenyl is, for example, propenyl, butenyl, hexenyl or octenyl.

Examples of suitable cycloalkyl radicals $R^2$ to $R^5$ are cyclopentyl, cyclohexyl, cycloheptyl, cyclopentenyl or cyclohexenyl.

Examples of aromatic radicals $R^2$ to $R^5$ are phenyl, benzyl, toluyl, phenylethyl, p-methylbenzyl or p-propylphenyl.

Examples of suitable radicals $R^6$ to $R^9$ are methoxy, ethoxy, n-propoxy, isopropoxy, n-butoxy, isobutoxy, tert-butoxy and hexyloxy, but two non-adjacent radicals $R^6$ to $R^9$ are each hydrogen.

The preparation of the starting materials of the formula (II) is described in, for example, DE-2 710 420.

In addition to ammonia, primary amines of the formula (III) which are capable of being vaporized without decomposition, for example methylamine, ethylamine, n-propylamine, isopropylamine, n-butylamine, isobutylamine, sec-butylamine, n-pentylamine, 3-methyl-1-butylamine, 3-methyl-2-butylamine, 2-methyl-2-butylamine, n-hexylamine, n-octylamine, 2-ethyl-1-hexylamine, cyclohexylamine, benzylamine, aniline, 2-phenylethylamine or toluidine, are suitable for the preparation of the corresponding pyrroles of the formula (I).

Examples of the end products (I) which can be prepared from the starting materials (II) and (III) are pyrrole, 1-methylpyrrole, 1-ethylpyrrole, 1-n-propylpyrrole, 1-isopropylpyrrole, 1-n-butylpyrrole, 1-isobutylpyrrole, 1-sec-butylpyrrole, 1-n-pentylpyrrole, 1-(3-methyl-1-butyl)-pyrrole, 1-(3-methyl-2-butyl)-pyrrole, 1-(2-methyl-2-butyl)-pyrrole, 1-n-hexylpyrrole, 1-n-octylpyrrole, 1-(2-ethyl-1-hexyl)-pyrrole, 1-cyclohexylpyrrole, 1-benzylpyrrole, 1-phenylpyrrole, 1-(2-phenylethyl)-pyrrole, 3-methylpyrrole, 3,4-dimethylpyrrole, 2-methylpyrrole, 2,4-dimethylpyrrole, 2,5-dimethylpyrrole, 1,2-dimethylpyrrole, 1,3-dimethylpyrrole, 1,2,4-trimethylpyrrole, 1,3,4-trimethylpyrrole, 1,2,5-trimethylpyrrole, 2-ethylpyrrole, 1-methyl-2-ethylpyrrole, 2-phenylpyrrole, 1-methyl-2-phenylpyrrole, 2-benzylpyrrole, 1-methyl-2-benzylpyrrole, 2-cyclohexylpyrrole and 2-(p-tolyl)-pyrrole.

The catalysts used for the novel process are acidic zeolite catalysts. Zeolites are crystalline aluminosilicates which have a highly ordered structure with a rigid three-dimensional network of $SiO_4$ and $AlO_4$ tetrahedra which are bonded by common oxygen atoms. The ratio of Si and Al atoms to oxygen is 1:2 (see Ullmanns Encyclopädie d. techn. Chemie, 4th Edition, Volume 24, page 575 (1983)). The electrovalency of the aluminum-containing tetrahedra is balanced by the inclusion of cations in the crystal, for example an alkali metal or hydrogen ion. Cation exchange is possible. The voids between the tetrahedra are occupied by water molecules prior to dehydration by drying or calcination.

In the zeolites, other elements, such as B, Ga, Fe, Cr, V, As, Sb, Bi or Be, or mixtures of these can be incorporated in the framework, instead of aluminum, or the silicon can be replaced by a tetravalent element, such as Ge, Ti, Zr or Hf.

Depending on their structure, zeolites are divided into various groups (see Ullmanns Encyclopädie d.

techn. Chemie, 4th Edition, Vol. 24, page 575 (1983)). For example, the zeolite structure is formed by chains of tetrahedra in the mordenite group or sheets of tetrahedra in the chabasite group, while in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made between zeolites of type A, L, X and Y.

Catalysts which are suitable for the novel process are zeolites of the mordenite group or fine-pore zeolites of the erionite or chabasite type or zeolites of the faujasite type, for example Y, X or L zeolites. This group of zeolites includes the ultrastable zeolites of the faujasite type, i.e. dealuminated zeolites. Processes for the preparation of such zeolites are described in Catalysis by Zeolites, Volume 5, from Studies in Surface Science and Catalysis, ed. B. Imelik et al., Elsevier Scientific Publishing Company, 1980, page 2103, and Crystal Structures of Ultrastable Faujasites, Advances in Chemistry Series No. 101, American Chemical Society Washington, D.C., page 226 et seq (1971) and in U.S. Pat. No. 4,512,961.

Zeolites of the pentasil type are particularly suitable. They possess, as a common building block, a 5-membered ring composed of $SiO_4$ tetrahedra. They have a high $SiO_2/Al_2O_3$ ratio and a pore size which is between that of the zeolites of type A and that of type X or Y (cf. Ullmanns Encyclopädie d. techn. Chem., 4th Edition, Vol. 24, 1983).

These zeolites may have different compositions. They are aluminosilicate, borosilicate, iron silicate, beryllium silicate, gallium silicate, chromium silicate, arsenosilicate, antimony silicate and bismuth silicate zeolites or mixtures of these, ad aluminogermanate, borogermanate, gallium germanate and iron germanate zeolites or mixtures of these. Aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali or alkaline earth, at from 100° to 220° C. under autogenous pressure. These include the isotactic zeolites according to European Patent Nos. 34,727 and 46,504. The aluminosilicate zeolites obtained have an $SiO_2/Al_2O_3$ ratio of from 10 to 40,000, depending on the amounts of starting materials chosen. These aluminosilicate zeolites can be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution with or, in particular, without the addition of an alkali or alkaline earth. These include the isotactic zeolites according to European Patent Nos. 34,727 and 46,504. Such borosilicate zeolites can also be prepared if the reaction is carried out in solution in an ether, eg. diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth at from 100° to 220° C. under autogenous pressure.

The silicon-rich zeolites ($SiO_2/Al_2O_3 \geq 10$) which can be used include the ZSM types, ferrierite, NU-1 and Silicalit ®, a molecular sieve, i.e. a silica polymorph.

The aluminosilicate, borosilicate and iron silicate zeolites prepared by this process can be isolated, dried at from 100° to 160° C., eg. 110° C., and calcined at from 450° to 550° C., eg. 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, in particular 75:25, silica, in particular finely divided $SiO_2$, mixtures of finely divided $SiO_2$ and finely divided $Al_2O_3$, $TiO_2$, $ZrO_2$, or clay. After the molding procedure, the extrudates or pellets are dried at 110° C. for 16 hours and calcined at 500° C. for 16 hours.

Suitable catalysts are also obtained if the aluminosilicate or borosilicate zeolite isolated is molded directly after drying and is not subjected to calcination until after the molding procedure. The aluminosilicate and borosilicate zeolites prepared can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example in the Na form, the latter can be completely or partially converted into the desired H form by ion exchange, for example with ammonium ions, and subsequent calcination, or by treatment with acids.

If, in the reaction, deactivation of the zeolite catalysts occurs as a result of coking, it is advisable to regenerate the zeolites by burning off the coke deposit with air or with an air/$N_2$ mixture at from 400° to 550° C., in particular 500° C. As a result, the zeolites regain their initial activity.

By precoking, it is possible to adjust the activity of the catalyst to obtain optimum selectivity with respect to the desired reaction product.

In order to obtain very high selectivity, high conversion and long catalyst lives, it may be advantageous to modify the zeolites. In a suitable method of modifying the catalysts, for example, the unmolded or molded zeolites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4 to 8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, and rare earth metals, such as La, Ce, Pr, Nd, Fr, Yb and U.

Advantageously, doping is carried out by a procedure in which, for example, the molded zeolite is initially taken in a riser tube and, for example, an aqueous or ammoniacal solution of a halide or of a nitrate of the metals described above is passed over the said zeolite at from 20° to 100° C. Ion exchange of this type can be carried out, for example, on the hydrogen, ammonium and alkali metal form of the zeolite. In another possible method of applying metals to the zeolites, the zeolite material is impregnated with, for example, a halide, a nitrate or an oxide of the stated metals in aqueous, alcoholic or ammoniacal solution. Both ion exchange and impregnation are followed by one or more drying steps and, if desired, repeated calcination.

In a possible embodiment, for example, $Cu(NO_3)_2 \cdot 3H_2O$ or $Ni(NO_3)_2 \cdot 6H_2O$ or $Ce(NO_3)_3 \cdot 6H_2O$ or $La(NO_3)_2 \cdot 6H_2O$ or $Cs_2CO_3$ is dissolved in water. This solution is used to impregnate the molded or unmolded zeolite for a certain time, for example 30 minutes. Any supernatant solution is freed from water in a rotary evaporator. Thereafter, the impregnated zeolite is dried at about 150° C. and calcined at about 550° C. This impregnating process can be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours, while stirring. After filtration, drying at about 150° C. and calcination at about 500° C., the zeolite material thus obtained can be further processed with or without a binder to give extrudates, pellets or fluidizable material.

The zeolite in the H form or ammonium form or alkali metal form can be subjected to ion exchange by a procedure in which the zeolite, in the form of extrudates or pellets, is initially taken in a column and an aqueous $Ni(NO_3)_2$ solution or ammoniacal $Pd(NO_3)_2$ solution is circulated over the said zeolite for from 15 to 20 hours at slightly elevated temperatures of from 30° to 80° C. The product is then washed thoroughly with water, dried at about 150° C. and calcined at about 550° C. In the case of some metal-doped zeolites, for example Pd-, Cu- or Ni-doped zeolites, an aftertreatment with hydrogen is advantageous.

In another possible method of modification, the molded or unmolded zeolite material is subjected to a treatment with acids, such as hydrochloric acid, hydrofluoric acid and phosphoric acid, and/or steam. In this procedure, for example, the zeolites in powder form can first be treated with 1N phosphoric acid for 1 hour at 80° C. After this treatment, the product is washed with water, dried at 110° C. for 16 hours and calcined at 500° C. for 20 hours. In another procedure, zeolites, before or after they have been molded with binders, are treated with a 3-25, in particular 12-20, % strength by weight aqueous hydrochloric acid, for example for from 1 to 3 hours at from 60° to 80° C. Thereafter, the zeolite treated in this manner is washed with water, dried, and calcined at from 400° to 500° C.

In a particular embodiment of the acid treatment, the zeolite material, before it has been molded, is treated at elevated temperatures with 0.001–2N, preferably 0.05–0.5N hydrofluoric acid, for example by refluxing for from 0.5 to 5, preferably from 1 to 3, hours. The zeolite material is isolated, for example by filtering it off and washing it thoroughly, and is then advantageously dried at from 100° to 160° C. and calcined at from 450° to 600° C. In another embodiment of the acid treatment, the zeolite material is molded with a binder and then treated at from 50° to 90° C., in particular from 60° to 80° C., for from 0.5 to 5 hours with 12-20% strength by weight hydrochloric acid. The zeolite material is then washed thoroughly, dried at from 100° to 160° C. and calcined at from 450° to 600° C. An HF treatment may also be followed by an HCl treatment.

In another procedure, the zeolites can be modified by applying phosphorus compounds, such as trimethoxy phosphate, trimethoxyphosphine, or primary, secondary or tertiary sodium phosphate. The zeolites, in the form of extrudates, pellets or fluidizable material, are impregnated with aqueous $H_3PO_4$ solution, dried at 110° C. and calcined at 500° C.

Further catalysts for the novel process are phosphates, in particular aluminum phosphates, silicon aluminum phosphates, silicon iron aluminum phosphates, cerium phosphate, zirconium phosphates, boron phosphate, iron phosphate and mixtures of these. In particular, aluminum phosphates which have been synthesized under hydrothermal conditions and have a zeolite structure are used as aluminum phosphate catalysts. The said aluminum phosphates are, for example, APO-5, APO-9, APO-11, APO-12, APO-14, APO-21, APO-25, APO-31 and APO-33. Syntheses of these compounds are described in European Patent No. 132,708 and U.S. Pat. Nos. 4,310,440 and 4,473,663.

$AlPO_4$-5 (APO-5) can be synthesized by mixing orthophosphoric acid with pseudoboehmite (Catapal SB ®) in water to give a homogeneous mixture, adding tetrapropylammonium hydroxide to this mixture and then carrying out the reaction at about 150° C. for from 20 to 60 hours under autogenous pressure in an autoclave. The $AlPO_4$ filtered off is dried at from 100° to 160° C. and calcined at from 450° to 550° C.

$AlPO_4$-9 (APO-9) can likewise be synthesized from orthophosphoric acid and pseudoboehmite but in aqueous DABCO solution (1,4-diazabicyclo[2.2.2]octane) at about 200° C. under autogenous pressure in the course of from 200 to 400 hours.

$AlPO_4$-21 (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates used for the novel process are, for example, SAPO-5, SAPO-11, SAPO-31 and SAPO-34. The synthesis of these compounds is described in European Patent No. 105,117 and U.S. Pat. No. 4,440,871. SAPOs are prepared by crystallization from an aqueous mixture at from 100° to 250° C. and under autogenous pressure in the course of from 2 hours to 2 weeks, the reaction mixture of a silicon, aluminum and phosphorus component being reacted in aqueous solutions containing organic amines.

SAPO-5 is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder is filtered off, dried at from 110° to 160° C. and calcined at from 450° to 550° C.

Precipitated aluminum phosphates can also be used as phosphate catalysts in the process. For the preparation of an aluminum phosphate of this type, for example 92 g of diammonium hydrogen phosphate are dissolved in 700 ml of water. 260 g of $Al(NO_3)_3 \cdot H_2O$ in 700 ml of water are added dropwise to this solution in the course of 2 hours. During this procedure, the pH is kept at 8 by the simultaneous addition of 25% strength $NH_3$ solution. The resulting precipitate is stirred for a further 12 hours and then filtered off under suction and washed thoroughly. It is dried at 60° C. for 16 hours.

Boron phosphates can be prepared, for example, by mixing and kneading concentrated boric acid and phosphoric acid and subsequently carrying out drying and calcination in an inert gas, air or steam atmosphere at from 250° to 650° C., in particular from 300° to 500° C.

Modifying components can be applied, as described for the zeolites, to these phosphates by impregnation (immersion and spraying) or in some cases also by ion exchange. As in the case of the zeolite catalysts, modification may also be effected with acids.

Examples of suitable acidic catalysts are the acidic oxides of elements of main groups III and IV and subgroups IV to VI of the Periodic Table, in particular oxides such as silica in the form of silica gel, kieselguhr or quartz, as well as titanium dioxide, zirconium dioxide, phosphorus oxides, vanadium oxides, niobium oxides, boron oxides, aluminas, chromium oxides, molybdenum oxides, tungsten oxides and pumice or mixtures of these oxides. These oxides may also be doped by the application of modifying components, as described for the zeolite catalysts. Treatment with acids, as described for the zeolite catalysts, is also a possible method of modification.

Catalysts impregnated with phosphoric acid or with boric acid can also be used. Phosphoric acid or boric acid is applied, for example, to $SiO_2$, $Al_2O_3$, $TiO_2$ or pumice carriers, for example by impregnation or spraying. A catalyst containing phosphoric acid can be obtained, for example, by impregnating $SiO_2$ with $H_3PO_4$ or $NaH_2PO_4$ or $Na_2HPO_4$ solution and then drying and calcining the product. However, phosphoric acid can also be sprayed together with silica gel in a spray tower; this is followed by drying and in general calcination. Phosphoric acid can also be applied to the carrier in an impregnating mill.

The catalysts described here may alternatively be used in the form of 2-4 mm extrudates, tablets of 3-5 mm diameter or chips having particle sizes of from 0.1 to 0.5 mm or in the form of a fluidized catalyst.

The conversion is preferably carried out in the gas phase at from 100° to 500° C., in particular from 200° to 400° C., and at a WHSV of from 0.1 to 20 $h^{-1}$, in particular from 0.5 to 5 $h^{-1}$ (g of starting material per g of catalyst per hour). The molar ratio of educt to ammonia or amine is from 1:0.5 to 1:20, preferably from 1:1 to 1:5. The reaction can be carried out in a fixed bed or fluidized bed.

It is also possible to carry out the reaction in the liquid phase (suspension, trickle-bed of liquid phase method) at from 50° to 200° C.

The process is, as a rule, carried out under atmospheric pressure or, depending on the volatility of the starting compound and products, under reduced or superatmospheric pressure, either batchwise or, preferably, continuously. The reaction can also be readily controlled under reduced pressure.

Sparingly volatile or solid starting materials are used in dissolved form, for example in solution in tetrahydrofuran, toluene or petroleum ether. In general, the starting material can be diluted with such solvents or with inert gases, such as $N_2$, Ar or steam. In particular cases, it is also possible to use $O_2$.

After the reaction, the resulting products are isolated from the reaction mixture by a conventional method, for example by distillation; unconverted starting materials are, if required, recycled to the reaction.

The gaseous reaction products are advantageously immediately introduced into a separation stage, for example into a fractionation column, and are separated into their individual components.

The pyrroles prepared by the novel process are useful starting materials for the preparation of dyes, corrosion inhibitors, drugs and pesticides.

EXAMPLES 1 TO 28

The reactions in the gas phase are carried out under isothermal conditions in a tube reactor (coil, 0.6 cm internal diameter, 90 cm length) in the course of 6 hours. The reaction products are isolated and characterized by conventional methods. Quantitative determination of the reaction products and of the starting materials is effected by gas chromatography.

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

This material is molded with a molding assistant to give 2 mm extrudates, which are dried at 110° C. for 16 hours and calcined at 500° C. for 24 hours.

Catalyst B

Catalyst B is obtained by molding the borosilicate zeolite of catalyst A with boehmite in a weight ratio of 60:40 to give 2 mm extrudates, which are dried at 110° C. for 16 hours and calcined at 500° C. for 24 hours.

Catalyst C

An aluminosilicate zeolite of the pentasil type is prepared under hydrothermal conditions, under autogenous pressure and at 150° C., from 65 g of finely divided $SiO_2$ and 20.3 g of $Al_2(SO_4)_3$. $18H_2O$ in 1 kg of an aqueous 1,6-hexanediamine solution (weight ratio 50:50) in a stirred autoclave. The crystalline reaction product is filtered off, washed thoroughly, dried at 110° C. for 24 hours and calcined at 500° C. for 24 hours. This aluminosilicate zeolite contains 91.6% by weight of $SiO_2$ and 4.6% by weight of $Al_2O_3$.

The catalyst is molded with a molding assistant to give 2 mm extrudates, which are dried at 110° C. for 16 hours and calcined at 500° C. for 24 hours.

Catalyst D

Catalyst D is obtained by impregnating catalyst B with an aqueous $La(NO_3)_3$ solution and then drying the product at 130° C. for 2 hours and calcining it at 540° C. for 2 hours. The La content is 3.2% by weight.

Catalyst E

Catalyst E is obtained by impregnating. the extrudates of catalyst B with an aqueous solution of cerium nitrate and then drying the product at 130° C. for 2 hours and calcining it at 540° C. for 2 hours. The Ce content is 2.5% by weight.

Catalyst F

The iron silicate zeolite of the pentasil type is synthesized under hydrothermal conditions, under autogenous pressure and at 165° C., from 273 g of waterglass, dissolved in 253 g of an aqueous 1,6-hexanediamine solution (weight ratio 50:50), and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. An iron silicate zeolite having an $SiO_2/Fe_2O_3$ ratio of 17.7 and an $Na_2O$ content of 1.2% by weight is obtained. The catalyst is extruded with finely divided $SiO_2$ in a weight ratio of 80:20 to give 2.5 mm extrudates, which are dried at 110° C. for 16 hours and calcined at 500° C. for 24 hours.

Catalyst G 660 g of silica sol (30% by weight of $SiO_2$) are mixed with 567 g of aqueous tetrapropylammonium hydroxide solution (20% strength) and reacted in an autoclave at 200° C. for 72 hours. After isolation from the mother liquor, the product is dried at 120° C. and calcined at 500° C. for 16 hours. The X-ray diffraction pattern is typical of Silicalit ®. This Silicalit is molded with finely divided $SiO_2$ in a weight ratio of 70:30 to give 2 mm extrudates, which are subjected to ion exchange with a 20% strength $NH_4Cl$ solution at 80° C. in a column. Thereafter, the product is washed thoroughly with water, dried at 110° C. and calcined for 5 hours at 500° C. The Na content of the Silicalit after this procedure is 0.015% by weight. The ion exchange can be repeated after intermediate calcination in order to obtain this Na content.

Catalyst H

Catalyst H is prepared in the same way as catalyst E, but catalyst H is impregnated with $Ce(NO_3)_3$. The Ce content is 3.4% by weight.

Catalyst I 100 g of the borosilicate zeolite used in catalyst A are treated with 280 ml of a 0.1N HF at 90° C. for 2 hours, filtered off and then dried at 160° C. This product is molded with amorphous aluminosilicate (25% by weight of $Al_2O_3$ and 75% by weight of $SiO_2$) in a weight ratio of 60:40 to give 2 mm extrudates, which are dried at 110° C. for 16 hours and calcined at 500° C. for 16 hours.

Catalyst J $AlPO_4$-5 (APO-5) is synthesized by stirring together 200 g of 95% strength phosphoric acid, dissolved in 325 g of $H_2O$, 136 g of boehmite and 678 g of tetrapropylammonium hydroxide (30% strength) and then carrying out the reaction at 150° C. under autogenous pressure in the course of 43 hours. The product dried at 120° C. and calcined for 16 hours at 500° C. contains 46.5% by weight of $P_2O_5$ and 45.5% by weight of $Al_2O_3$. This $AlPO_4$—5 is molded with boehmite in a weight ratio of 60:40 to give 2 mm extrudates, which are dried at 110° C. and calcined for 16 hours at 500° C.

Catalyst K

Silicon aluminum phosphate-5 (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 150° C. for 168 hours under autogenous pressure. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

Catalyst L

Commercial zirconium phosphate $Zr_3(PO_4)_4$ is molded in pure form.

Catalyst M $CePO_4$ is obtained by precipitation from 52 g of $Ce(NO_3)_3 \cdot 6H_2O$ and 56 g of $NaH_2PO_4 \cdot 2H_2O$. The material is filtered off and then molded to give extrudates, which are dried at 120° C. and calcined at 450° C. Catalyst M contains 47.1% by weight of Ce and 12.7% by weight of P.

Catalyst N $BPO_4$ is prepared by combining 49 g of $H_3BO_3$ with 117 g of $H_3PO_4$ (75% strength) in a kneader, evaporating excess water and molding the reaction product to give 3 mm extrudates. These extrudates are dried at 100° C. and calcined at 350° C. Catalyst N contains 8.77% by weight of B and 28.3% by weight of P.

Catalyst O

Catalyst O is a precipitated aluminum phosphate, which is obtained by precipitation from $Al(NO_3)_3/H_3PO_4$ solution using $NH_3$ at pH 6–7. The precipitate is filtered off, dried at 110° C. and calcined at 500° C. Catalyst O contains 28.5% by weight of Al and 13.2% by weight of P.

Catalyst P

Commercial NaY zeolite is extruded with boehmite in a weight ratio of 60:40 to give 2 mm extrudates, which are dried at 110° C. for 16 hours and calcined at 540° C. for 24 hours and subjected to ion exchange with 20% strength aqueous $La(NO_3)_2$ solution at 80° C. for 2 hours. After drying at 110° C. and calcination at 500° C., the La content should be 7.1% by weight and the Na content 1.1% by weight. Ion exchange can be repeated after intermediate calcination until the above values are reached.

Catalyst Q $SiO_2$, commercially available as D 11-10 ®.

Catalyst R $TiO_2$ P 25 ® is molded to give 2 mm extrudates, which are dried at 110° C. and calcined at 500° C. for 16 hours.

Catalyst S

Silica gel is treated with 85% strength $HPO_4$ and $H_3BO_3$ in a spray tower. The spray powder is molded to give pellets, which are dried at 120° C. and calcined for 16 hours at 500° C. Catalyst S contains 85.9% by weight of $SiO_2$, 1.56% by weight of P and 0.06% by weight of B.

Catalyst T $Al_2O_3$, commercially available as D 10-10 ®.

Catalyst U

D 10-10 is impregnated with $H_2BO_3$, dried at 110° C. and calcined for 5 hours at 550° C. Catalyst U is composed of 85% of $Al_2O_3$ and 15% of $B_2O_3$.

Catalyst V

Catalyst V is obtained by treating D 10-10 Al₂O₃ with 85% strength H₃PO₄ for 30 minutes and then drying the product at 130° C. for 2 hours and calcining it at 540° C. for 2 hours. The P content is 4.9% by weight.

Catalyst W 200 g of catalyst R are treated with 600 ml of 15% strength HCl at 80° C. for 1 hour. The material is then washed Cl-free, dried at 110° C. and calcined for 1 hour at 600° C.

The experimental results obtained with these catalysts and the experimental conditions are summarized in Tables 1 to 3.

It can be seen that, among the stated catalysts, the zeolite catalysts are most suitable for the novel process.

TABLE 1

1,4-dimethoxytetrahydrofuran (I) + NH₃ → pyrrole (II) + H₂O + 2CH₃OH

| Example | 1 | 2 | 3 | 4 | 5 |
|---|---|---|---|---|---|
| Catalyst | A | C | F | I | G |
| Temperature °C. | 400 | 400 | 400 | 350 | 400 |
| WHSV h⁻¹ | 3 | 3 | 3 | 3 | 3 |
| Molar ratio I:NH₃ | 1:3 | 1:3 | 1:3 | 1:3 | 1:3 |
| Conversion (I) | 100 | 100 | 100 | 98.8 | 100 |
| Selectivity (II) | 85.7 | 80.5 | 79.0 | 84.5 | 68.4 |

TABLE 2

1,4-dimethoxytetrahydrofuran (I) + NH₃ → pyrrole (II) + H₂O + 2CH₃OH

| Example | 6 | 7 | 8 | 9 | 10 | 11 | 12 | 13 | 14 |
|---|---|---|---|---|---|---|---|---|---|
| Catalyst | B | B | D | E | H | I | K | L | M |
| Temperature °C. | 300 | 350 | 350 | 350 | 350 | 400 | 400 | 400 | 400 |
| WHSV h⁻¹ | 3 | 3 | 3 | 3 | 3 | 3 | 3 | 3 | 3 |
| Molar ratio I:NH₃ | 1:3 | 1:3 | 1:3 | 1:3 | 1:3 | 1:3 | 1:3 | 1:3 | 1:3 |
| Composition of the liquid product mixture in % by area | | | | | | | | | |
| I | 26.7 | — | — | — | — | 13.8 | 1.5 | 36.9 | 37.6 |
| II | 47.8 | 63.9 | 67.4 | 64.3 | 63.9 | 42.4 | 69.4 | 25.3 | 31.8 |
| CH₃OH | 18.1 | 22.1 | 24.1 | 21.3 | 21.9 | 21.8 | 24.8 | 15.8 | 13.0 |
| Methoxydihydrofuran | 2.7 | 5.6 | 4.2 | 7.1 | 5.9 | 5.1 | 1.8 | 9.4 | 5.0 |
| N—methylpyrrole | 1.9 | — | 1.7 | 2.5 | — | 0.7 | 0.8 | 0.2 | 2.6 |
| Remainder* | 2.8 | 8.4 | 2.6 | 4.8 | 8.3 | 16.2 | 1.7 | 12.4 | 10.0 |

| Example | 15 | 16 | 17 | 18 | 19 | 20 | 21 | 22 | 23 | 24 |
|---|---|---|---|---|---|---|---|---|---|---|
| Catalyst | N | O | P | Q | R | S | T | U | V | W |
| Temperature °C. | 400 | 400 | 350 | 400 | 400 | 400 | 400 | 400 | 400 | 400 |
| WHSV h⁻¹ | 3 | 3 | 3 | 3 | 3 | 3 | 3 | 3 | 3 | 3 |
| Molar ratio I:NH₃ | 1:3 | 1:3 | 1:3 | 1:3 | 1:3 | 1:3 | 1:3 | 1:3 | 1:3 | 1:3 |
| Composition of the liquid product mixture in % by area | | | | | | | | | | |
| I | 30.4 | 8.3 | 21.0 | 0.4 | 52.4 | 0.6 | 4.5 | 4.9 | 14.0 | 59.6 |
| II | 36.2 | 45.5 | 44.1 | 43.3 | 29.7 | 55.1 | 52.7 | 53.5 | 45.6 | 22.3 |
| CH₃OH | 7.7 | 25.3 | 20.6 | 30.4 | 10.5 | 26.6 | 23.3 | 25.1 | 17.5 | 8.8 |
| Methoxydihydrofuran | 4.7 | 4.6 | 5.2 | 8.9 | 4.6 | 1.4 | 2.2 | 2.7 | 3.0 | 6.0 |
| N—methylpyrrole | 12.5 | 2.2 | 0.8 | 0.3 | 0.1 | 6.8 | 0.6 | 4.3 | 6.6 | — |
| Remainder* | 8.5 | 14.1 | 8.3 | 17.0 | 2.7 | 9.5 | 16.7 | 9.5 | 13.3 | 3.3 |

*Not identified

TABLE 3

2-methylpyrrole from 2-methyl-2,5-dimethoxytetrahydrofuran and NH₃

| Example | 25[1] | 26[1] | 27[1] | 28[1] |
|---|---|---|---|---|
| Catalyst | B | E | I | C |
| Molar ratio educt/NH₃ | 2.5 | 2.5 | 2.5 | 2.5 |
| Temp. °C. | 350 | 350 | 350 | 350 |
| WHSV h⁻¹ | 1.5 | 1.5 | 1.5 | 1.5 |
| Conversion | 100 | 100 | 100 | 100 |
| Selectivity | 68.9 | 71.4 | 82.3 | 66.5 |

[1] 2-methyl-2,5-dimethoxytetrahydrofuran dissolved in tetrahydrofuran (50:50)

We claim:

1. A process for preparing a pyrrole of the formula I

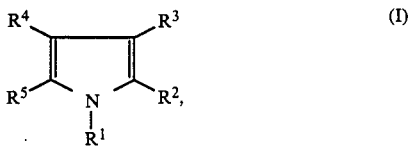

which comprises: reacting a dialkoxytetrahydrofuran of the formula II

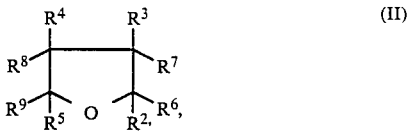

where $R^2$ to $R^5$ in the formulae (I) and (II) are identical or different and are each hydrogen, a straight-chain or branched alkyl or alkenyl radical of not more than 12 carbon atoms, a cycloalkyl or cycloalkenyl radical of 5 to 8 carbon atoms, an aryl, alkylaryl or aralkyl radical of 6 to 16 atoms, and two non-adjacent radicals $R^6$ to $R^9$ are alkoxy and the other two radicals $R^6$ to $R^9$ are hydrogen, with ammonia or a primary amine $H_2NR^1$, where $R^1$ in formula (I) is hydrogen, alkyl, aryl, alkylaryl, aralkyl or cycloalkyl, in the presence of an acidic, solid, oxide or phosphate catalyst.

2. The process of claim 1, wherein the catalyst used is a zeolite.

3. The process of claim 1, wherein the catalyst used is a zeolite of the pentasil type.

4. The process of claim 1, wherein the catalyst used is an aluminosilicate, borosilicate or iron silicate zeolite of the pentasil type.

5. The process of claim 1 wherein the catalyst used is a zeolite of the faujasite type.

6. The process of claim 1, wherein the catalyst used is a zeolite doped with alkali metals, transition metals or rare earth metals.

7. The process of claim 1, wherein the catalyst used is an acidic, solid phosphate catalyst selected from the group consisting of: aluminum phosphates, silicon aluminum phosphates, silicon iron aluminum phosphates, cerium phosphate, zirconium phosphates, boron phosphate, iron phosphate and mixtures thereof.

8. The process of claim 1, wherein the catalyst used is an acidic alumina phosphate or a silica-alumina phosphate having a zeolite structure.

9. The process of claim 1, wherein the catalyst used is an acidic oxide of the elements Si, Ti, Zr, B, Fe, W, Mo, Nb or V.

10. The process of claim 1, wherein the reaction is carried out in the gas phase.

* * * * *